(12) United States Patent
Larsen

(10) Patent No.: US 12,253,510 B2
(45) Date of Patent: Mar. 18, 2025

(54) IN-GROUND WIRELESS SOIL MOISTURE SENSOR

(71) Applicant: Smart Rain Systems, LLC, Centerville, UT (US)

(72) Inventor: Rudy Lars Larsen, Bountiful, UT (US)

(73) Assignee: SMART RAIN SYSTEMS, LLC, Centerville, UT (US)

( * ) Notice: Subject to any disclaimer, the term of this patent is extended or adjusted under 35 U.S.C. 154(b) by 0 days.

(21) Appl. No.: 18/141,848

(22) Filed: May 1, 2023

(65) Prior Publication Data

US 2023/0384284 A1 Nov. 30, 2023

Related U.S. Application Data

(63) Continuation of application No. 17/725,836, filed on Apr. 21, 2022, now Pat. No. 11,674,944.

(60) Provisional application No. 63/177,720, filed on Apr. 21, 2021.

(51) Int. Cl.
*G01D 11/24* (2006.01)
*G01N 33/24* (2006.01)

(52) U.S. Cl.
CPC .......... *G01N 33/246* (2013.01); *G01D 11/24* (2013.01)

(58) Field of Classification Search
CPC ...................................................... G01D 11/24
See application file for complete search history.

(56) References Cited

U.S. PATENT DOCUMENTS

| D841,490 S | 2/2019 | Boedhoe et al. | |
| 2015/0096368 A1* | 4/2015 | O'Brien | E02D 1/00 73/32 R |
| 2020/0084520 A1* | 3/2020 | Ham | H04B 17/318 |
| 2020/0396915 A1* | 12/2020 | Guidish | A01G 25/167 |

FOREIGN PATENT DOCUMENTS

| CN | 104034861 | | 9/2014 | |
| CN | 104034861 A | * | 9/2014 | ......... G01N 21/3554 |
| CN | 215727476 | | 2/2022 | |
| CN | 215727476 U | * | 2/2022 | |
| FR | 3092403 | | 8/2020 | |
| FR | 3092403 A1 | * | 8/2020 | ............. G01K 13/00 |

OTHER PUBLICATIONS

U.S. Appl. No. 17/725,836, filed Feb. 3, 2023, Notice of Allowance.
U.S. Appl. No. 17/725,836, filed May 24, 2023, Issue Notification.

\* cited by examiner

*Primary Examiner* — Jamel E Williams
(74) *Attorney, Agent, or Firm* — RAY QUINNEY & NEBEKER; Thomas L. Lingard

(57) ABSTRACT

An in-ground wireless moisture sensor may include one or more ultrasonic sensors in communication with a processor and a wireless communications module. The sensor may be powered by a power source, such as one or more rechargeable batteries as well as a solar panel in the cover of the sensor. Ultrasonic sensors may allow for wireless sensing of in-ground soil moisture levels at a distance farther than traditional sensors and therefore may give more accurate measurements. Methods for use and installation of the in-ground sensor, including a selectively removable cover, are described.

20 Claims, 14 Drawing Sheets

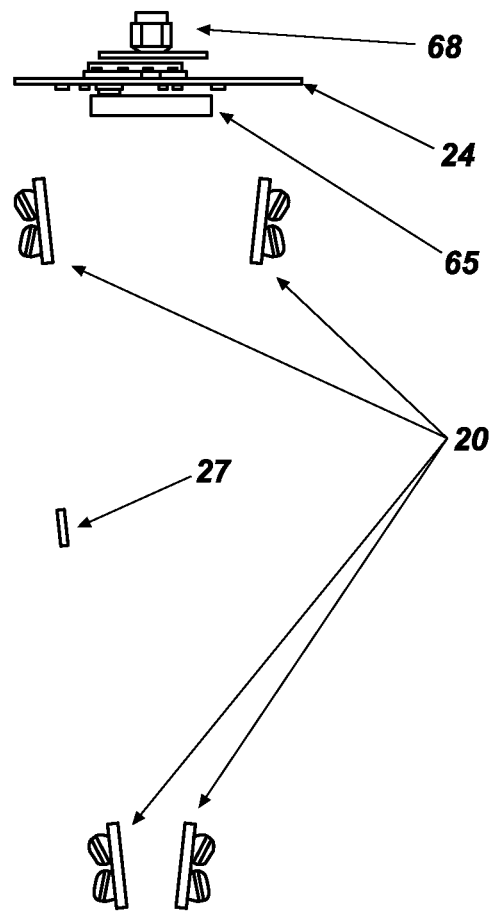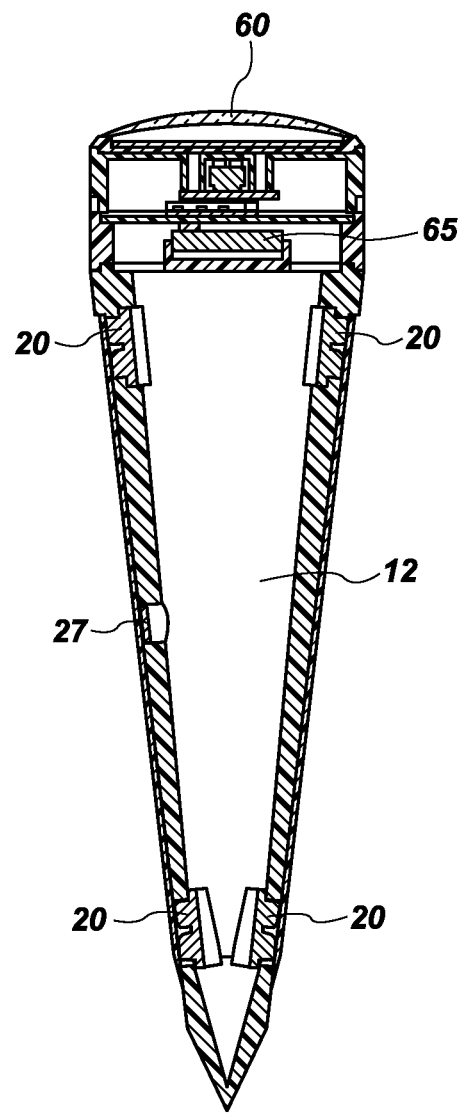
FIG. 11A                    FIG. 11B

105 Optional: Drill initial Depth Hole
110 Hammer in Smart Rain Moisture Sensor on black rubber cap to desired depth, either surface flush or exposed
115 Remove rubber cap
120 Screw on Solar Antenna Cap so finished sensor is either sub flush or exposed
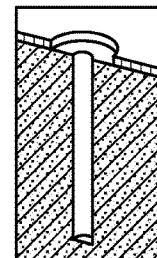 105
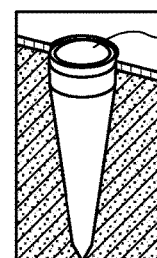 55
110
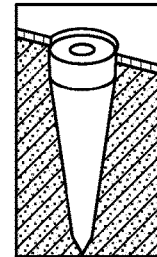 115
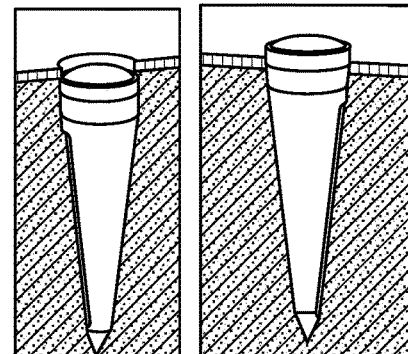
120a  120b
*FIG. 13A*  *FIG. 13B*

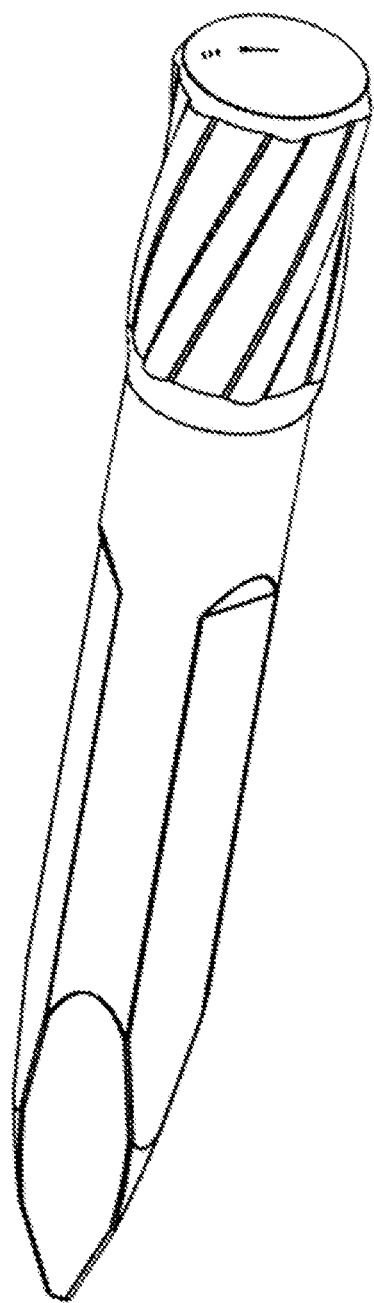
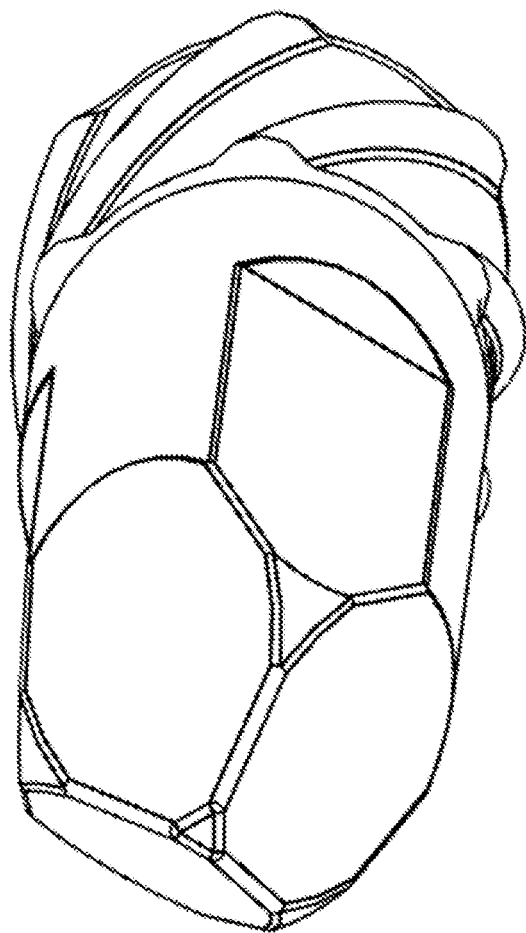
*FIG. 15A*  *FIG. 15B*

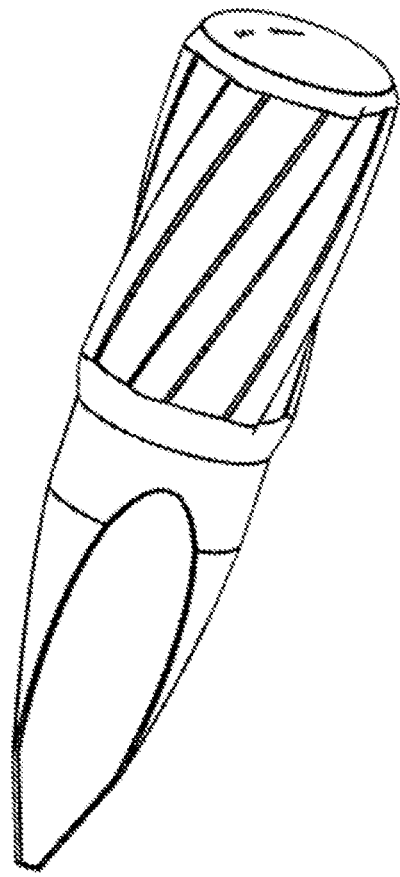
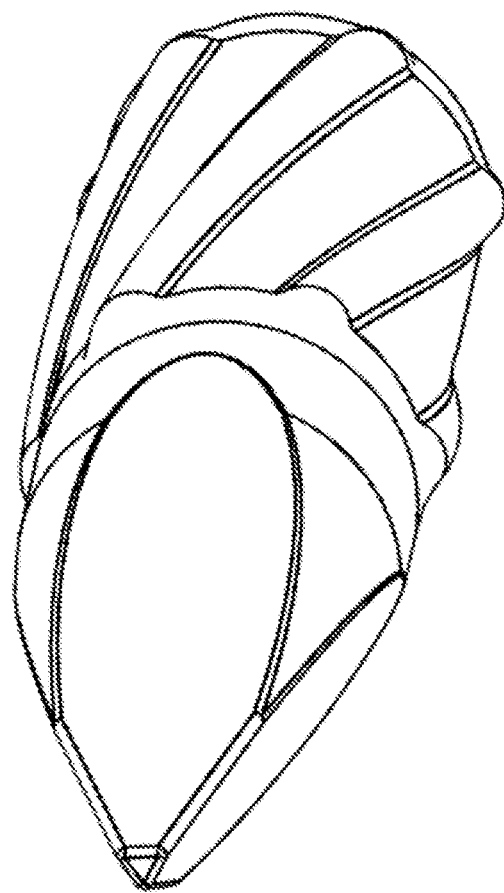
FIG. 16A
FIG. 16B

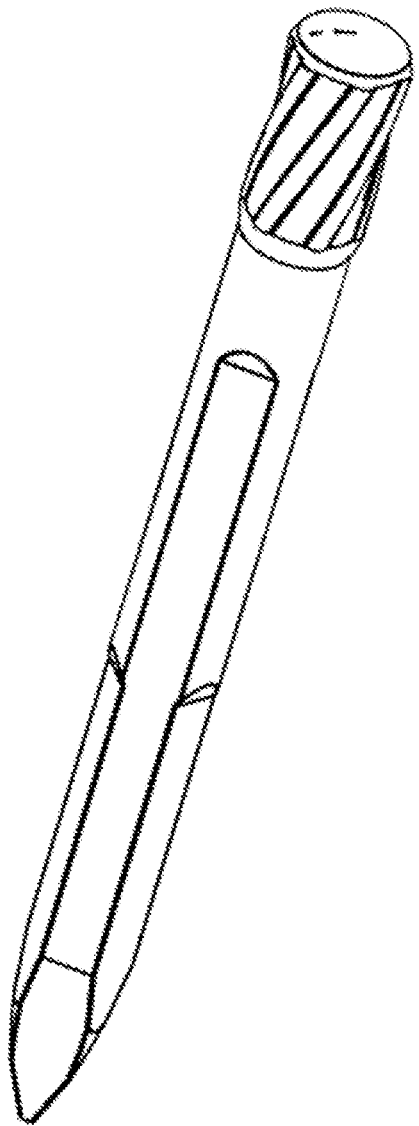
FIG. 17A
FIG. 17B

IN-GROUND WIRELESS SOIL MOISTURE SENSOR

CROSS REFERENCE TO RELATED MATTER

This application is a continuation of U.S. patent application Ser. No. 17/725,836, filed Apr. 21, 2022, which claims the benefit of and priority to U.S. Provisional Patent Application No. 63/177,720, titled IN-GROUND WIRELESS SOIL MOISTURE SENSOR filed Apr. 21, 2021, the entireties are hereby incorporated herein.

FIELD

This disclosure relates generally to a moisture sensor for investigating or analyzing materials, such as soil. The moisture sensor may use a combination of capacitance, ultrasound, and/or temperature to analyze soil moisture content.

BACKGROUND

Controllers for irrigation systems make it easier on property owners to water their landscapes. Simple systems for watering may include a start time and finish time for specific zones for a given landscape.

Smart controllers have become more and more common in the irrigation industry. Smart controllers and smart controller technology allows for a user to quickly and effectively make changes to an irrigation system, or system. Many irrigation systems that are controlled by smart controllers include one or more hardware devices for determining the status of the soil, such as a water flow detector, soil moisture sensor, local weather station, etc.

Soil moisture sensors may use various types of measurements to approximate moisture levels in the soil. For example, light may be reflected to the soil sample and the measured reflectance factor can be used to compute the moisture. More recently, capacitance-type sensors have become popular in determining soil moisture level.

The moisture content of soil is important to the efficient use and preservation of the soil and water. Monitoring the moisture content of the soil is important for enabling the estimation of soil water evaporation and run-off rates and for scheduling irrigation. While various techniques have been employed in the past to measure soil moisture, for various generally well-known reasons, none has proven altogether satisfactory.

Thus, there is a need for a soil moisture sensor that accurate, powered by a low voltage and consume minimal amounts of power when in use, and also able to wirelessly transmit data across a large distance to an irrigation controller.

SUMMARY

One aspect of the present disclosure is directed to a system for analyzing soil moisture levels, the system comprising: a sensor housing being generally hollow and formed of a wall having an inner side and an outer side, the sensor housing having a lower end to be inserted into soil, and an upper end, the sensor housing being tapered from the upper end to the lower end and diminishing in thickness towards the lower end; a processor located in the sensor housing, the processor in communication with an upper ultrasonic sensor, a lower ultrasonic sensor, and at least one temperature sensor; a wireless communications module in communication with the processor; the sensor housing having an upper opening for receiving the upper ultrasonic sensor, the upper opening extending from the inner side to the outer side of the wall of the sensor housing, the sensor housing having a central opening for receiving the lower ultrasonic sensor, the central opening extending from the inner side to the outer side of the wall of the sensor housing; and the sensor housing having a lower opening for receiving the lower ultrasonic sensor, the lower opening extending from the inner side to the outer side of the wall of the sensor housing.

In some configurations, the processor receives soil moisture data from the upper ultrasonic sensor and the lower ultrasonic sensor. The processor may receive soil temperature data from the temperature sensor. The wireless communications module may communicate or transmit the soil moisture data and the soil temperature data to a remote controller. In one specific configuration, the wireless communications module comprises a LoRa transceiver. Other wireless protocols may be used.

In some configurations, the housing is provided with an acoustically transparent material covering the upper opening, central opening, and lower opening.

According to another aspect, the system includes a power source in communication with at least the processor. The power source may comprise a rechargeable lithium-ion battery for wireless operation. In some configurations, a removable cover may be placed over the upper end of the sensor housing, the removable cover comprising a solar panel for converting sunlight to power, the solar panel in electrical communication with the power source. The removable cover may comprise an antenna in the removable cover for wireless communications, the antenna in communication with the processor. In some configurations, the system may include a removable cover for installation of the generally hollow sensor housing, the removable cover for installation formed of a resilient material.

According to yet another aspect, a system for analyzing a soil moisture level is disclosed, the system comprising: a soil moisture sensor comprising at least one ultrasonic sensor in communication with a wireless communications module, the ultrasonic sensor for generating ultrasonic signals and detecting one or more reflectance values of the ultrasonic signals; and a reflectance wave analyzer module in communication with the ultrasonic sensor, the reflectance wave analyzer module programmed to receive reflectance values of the ultrasonic signals, and based on pre-programmed baseline data and the one or more reflectance values, determine the soil moisture level.

The system may further comprise an irrigation system with one or more sprinklers; a processor in communication with the reflectance wave analyzer module and the one or more sprinklers, the processor configured to receive the soil moisture level from the reflectance wave analyzer module; and a storage medium storing instructions that, when executed, configure the processor to send a signal to an irrigation system to water more or water less based on the soil moisture level. According to another aspect, the system may comprise a centralized irrigation controller in communication with the wireless communications module and the reflectance wave analyzer module.

According to yet another aspect, a system for analyzing a soil moisture level is disclosed, the system comprising: a sensor housing having a lower end to be inserted into soil, and an upper end for connection to a cap; a processor located in the sensor housing, the processor in communication with at least one ultrasonic sensor; a wireless communications module in communication with the processor; a power source in communication with the processor, the power source comprising a rechargeable battery for wireless operation; and a cover for connection to the upper end of the sensor housing comprising a solar panel for converting sunlight to power, the solar panel in electrical communication with the power source.

In some configurations, the system may include at least one temperature sensor in communication with the processor. The at least one ultrasonic sensor may comprise a first ultrasonic sensor and a second ultrasonic sensor, the first ultrasonic sensor more proximal to the upper end of the sensor housing and the second ultrasonic sensor more proximal to the lower end of the sensor housing.

In some aspects, the sensor housing comprises an upper opening for receiving the first ultrasonic sensor and a lower opening for receiving the second ultrasonic sensor. The cover may be selectively removable and may be connected to the upper end of the sensor housing after the sensor housing is placed in soil. The cover may include one or more aspects of the system that may be subject to installation damage, such as a solar panel, a wireless communications antenna, etc. In other configurations, the power source is in electrical communication with a thermoelectric cooler for providing a charge to the power source.

BRIEF DESCRIPTION OF THE DRAWINGS

FIG. 11A is a front view of the electronics of an exemplary sensor, with the housing removed for clarity to show placement of the electronics relating to the housing.

FIG. 11B is a front, cross-sectional view of the exemplary sensor of FIG. 11A using ultrasonic sensors.

FIG. 13A is a flow diagram of an exemplary process for installing an in-ground soil moisture sensor.

FIG. 13B is an illustrative flow diagram showing cross-sectional views of the ground during the process steps of the flow diagram of FIG. 13A.

FIG. 15A is a top perspective view of another configuration of the in-ground soil moisture sensor.

FIG. 15B is a bottom perspective view of another configuration of the in-ground soil moisture sensor.

FIG. 16A is a top perspective view of another configuration of the in-ground soil moisture sensor.

FIG. 16B is a bottom perspective view of another configuration of the in-ground soil moisture sensor.

FIG. 17A is a top perspective view of another configuration of the in-ground soil moisture sensor.

FIG. 17B is a bottom perspective view of another configuration of the in-ground soil moisture sensor.

DETAILED DESCRIPTION

Figure 1:
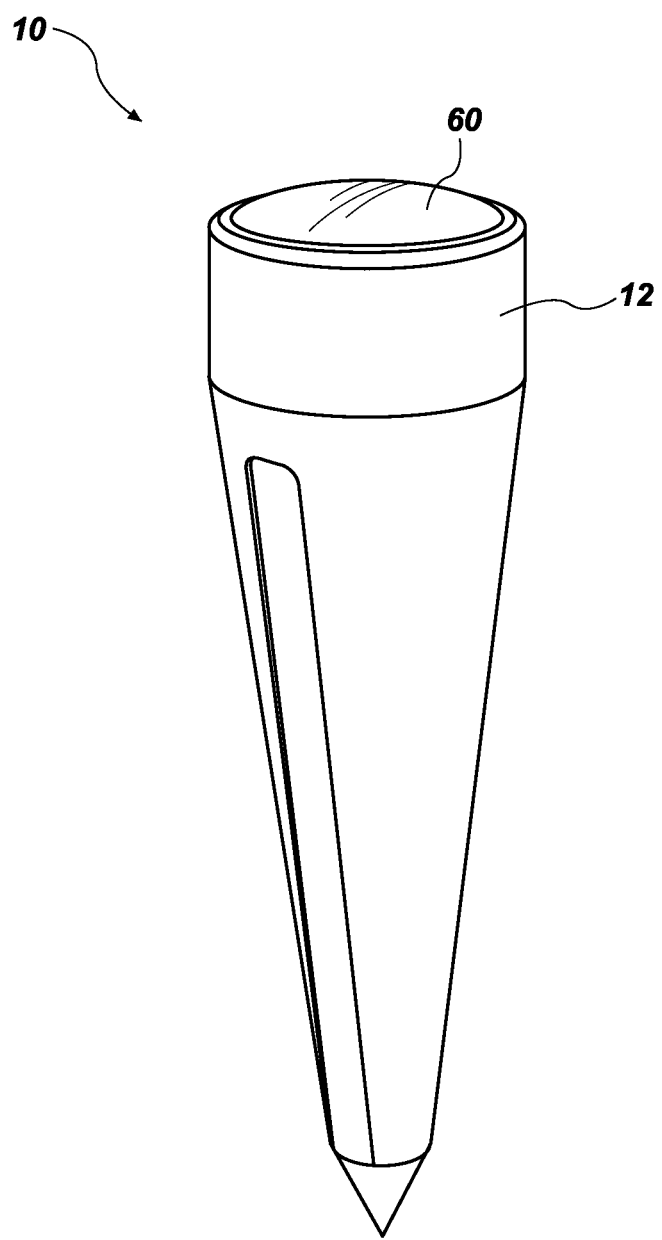
FIG. 1 is a perspective view of an in-ground soil moisture sensor as disclosed herein.
Figure 2:
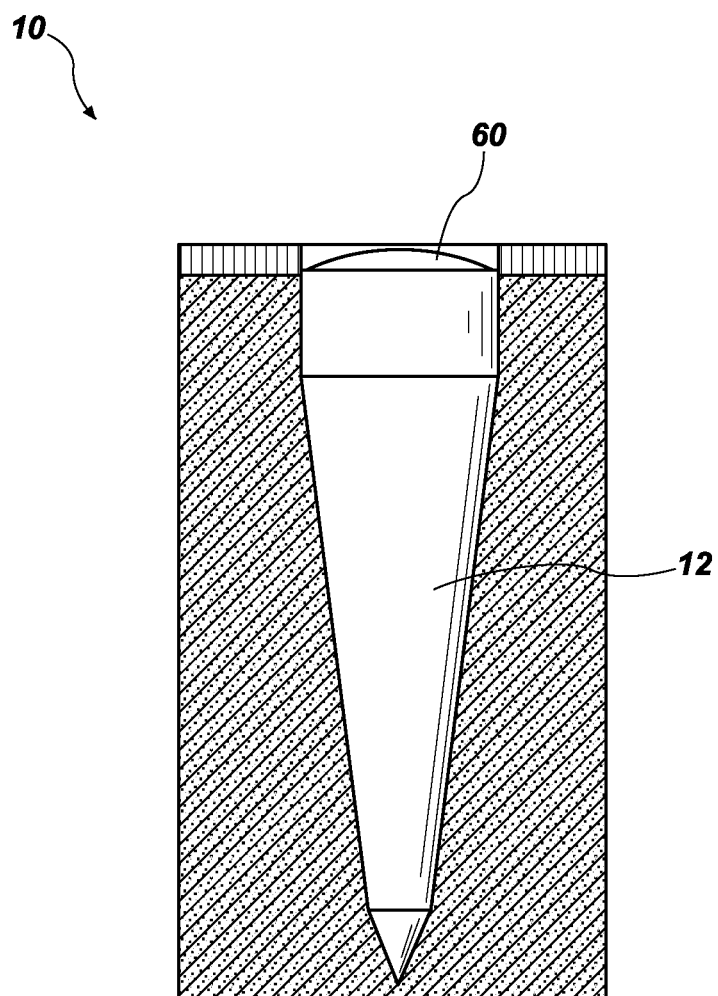
FIG. 2 is a side view of the in-ground soil moisture sensor of FIG. 1 shown in place in soil.

Before the present invention is disclosed and described in detail, it should be understood that the present disclosure is not limited to any particular structures, process steps, or materials discussed or disclosed herein, but is extended to include equivalents thereof as would be recognized by those of ordinary skill in the relevant art. More specifically, the invention is defined by the terms set forth in the claims. The discussion of any particular aspect of the invention is not to be understood as a requirement that such aspect must be present apart from an express inclusion of the aspect in the claims. As used in this specification and the appended claims, singular forms such as "a," "an," and "the" may include the plural unless the context clearly dictates otherwise. Thus, for example, reference to "a watering instruction" may include one or more of such watering instructions, and reference to "the moisture sensor" may include reference to one or more of such moisture sensors.

In the present document, the word "exemplary" is used herein to mean "serving as an example, instance, or illustration." Any embodiment or implementation of the present subject matter described herein as "exemplary" is not necessarily to be construed as preferred or advantageous over other embodiments. It will also be appreciated by those skilled in the art that the words during, while, and when as used herein are not exact terms that mean an action takes place instantly upon an initiating action but that there may be some small but reasonable delay, such as a propagation delay, between the initial action and the reaction that is initiated by the initial action. Additionally, the word "connected" and "coupled" is used throughout for clarity of the description and can include either a direct connection or an indirect connection. The word "generally" means substantially, mostly, mainly, essentially and/or largely.

The following description sets forth an ultrasonic moisture sensor or capacitance moisture sensor that may be used, for example, in an irrigation system, for managing irrigation and watering either residentially, commercially or agriculturally. The system may include multiple inputs from a plurality of sources to appropriately provide enough information to the system so that the ideal amount of moisture to a landscape is administered. One such input may be from a moisture sensor as described herein.

As used herein, "ultrasonic sensor" means a device that includes an ultrasonic transducer to send and receive ultrasonic pulses or soundwaves. An ultrasonic sensor may comprise a single transducer, or one or more transducers. Any suitable ultrasonic sensor may be used. For example, self-cleaning ultrasonic sensors can be used to reduce the impact of condensation and frost. Other suitable types of ultrasonic sensors may include HC-SR04 UHZ-AP-0A ultrasonic proximity sensor, Ultrasonic Transmitter Module and Receiver Modules, Waterproof Transmitters/receivers, TCT40-16R/T matched-pair ultrasonic transmitter and receiver, etc. Other known ultrasonic sensors may also be used. Suitable capacitance sensors such as those known in the art may also be used to provide a capacitance-type moisture sensor.

FIGS. 1-5 show an exemplary moisture sensor 10 that includes one or more ultrasonic sensors to determine soil moisture content. The moisture sensor 10 may generally consist of an outer housing 12 that houses components such as one or more ultrasonic sensors 20, a processor 24, a temperature sensor 27, and a wireless communications module 30.

The housing 12 in some configurations may be a generally hollow sensor housing, formed of a wall 32 with an inner side 32a and an outer side 32b. The housing 12 may be configured for insertion into soil, with a lower end 35 to be inserted first into the soil. The upper end 38 may either extend partially above the soil, or it may be flush with the soil level or slightly below the level of the soil. The housing 12 may be tapered from the upper end 38 to the lower end 35, diminishing in thickness towards the lower end 35. This tapered or "carrot" shape may allow the housing 12 to be more easily inserted into soil, and by pushing the soil away as it is inserted, it may also improve the contact between the soil and one or more sensors within the housing 12. The taper of the housing may be more or less extreme (such as a slight taper or a greater taper). Additionally, the housing can have other features on the exterior to help place the sensor into soil and/or help ensure the sensor remains in place. For example, threads may be provided on at least a portion of the housing to help keep the sensor housing in place in the soil (see alternate configurations illustrated in FIGS. 15A-17B). Other shapes of the housing 12 may also be used, such as a cylindrical shape, a cylindrical shape with a pointed lower end, etc., and all such alternate shapes are contemplated herein.

Figure 3:
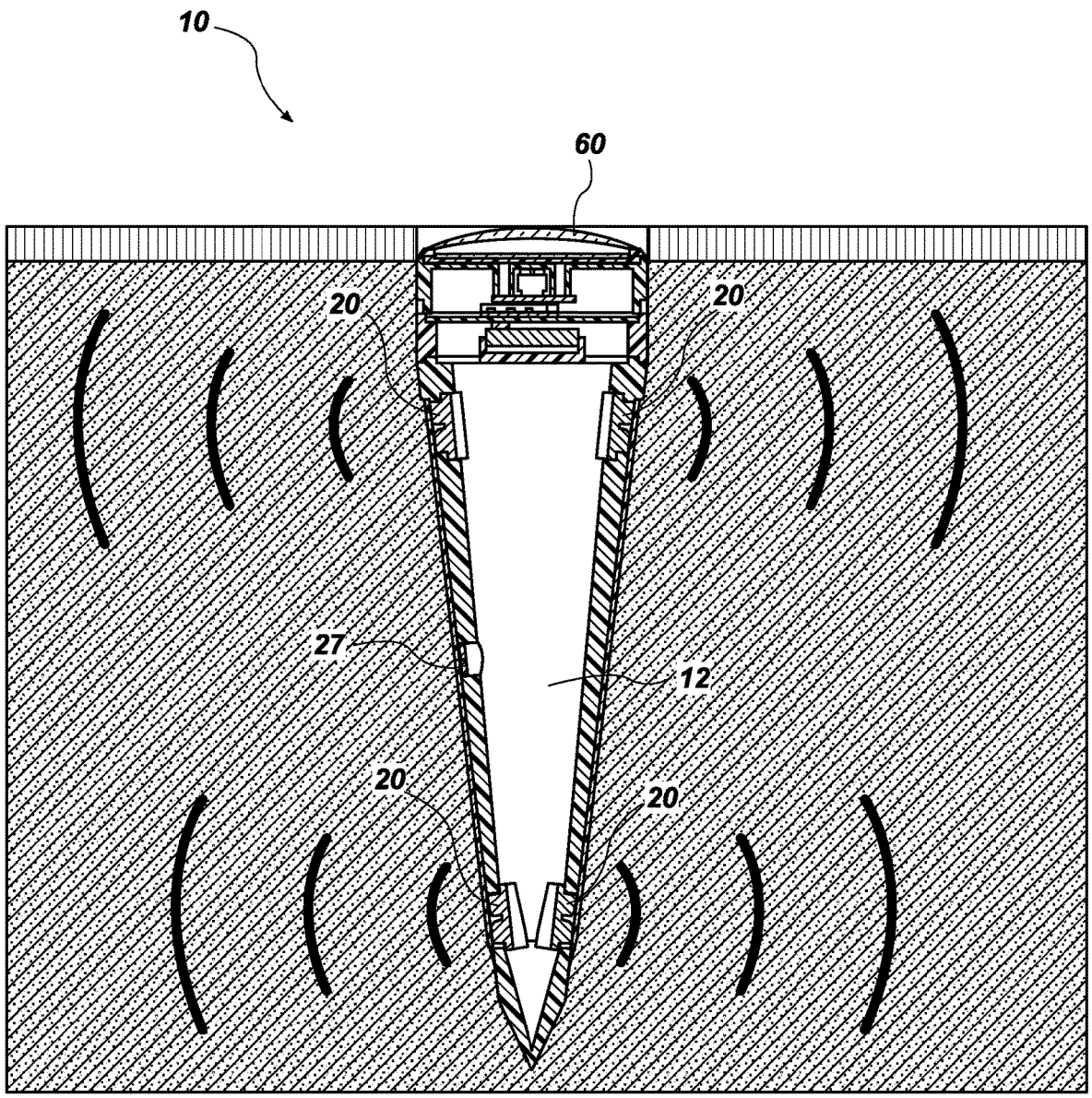
FIG. 3 is a side cross-sectional view of the in-ground soil moisture sensor of FIG. 2.
Figure 4:
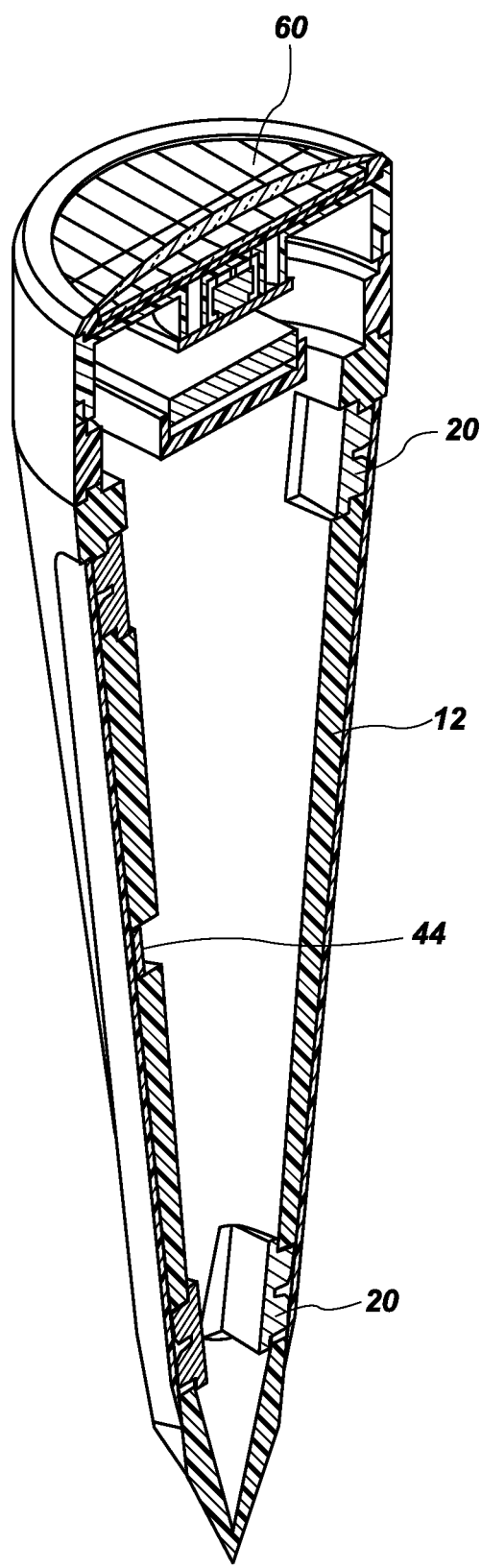
FIG. 4 is a perspective cross-sectional view of the in-ground soil moisture sensor of FIGS. 1-3.
Figure 5:
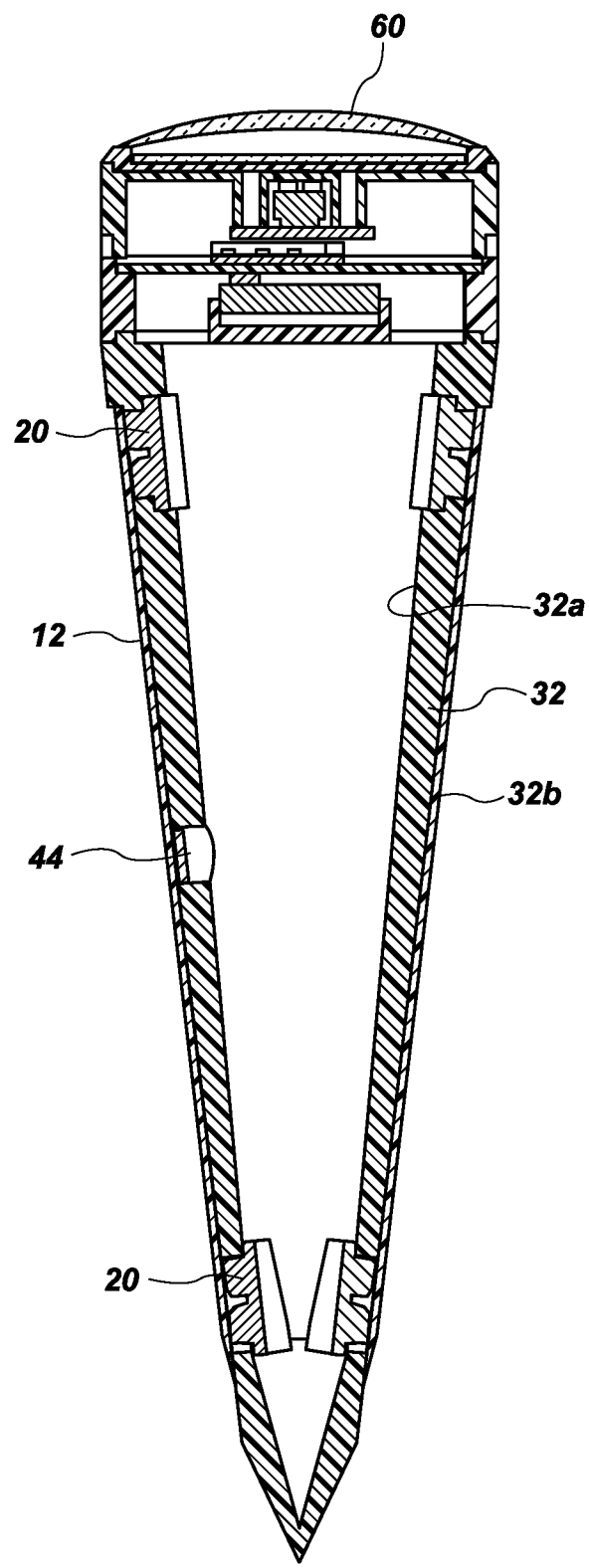
FIG. 5 is a side cross-sectional view of the in-ground soil moisture sensor of FIG. 4.
Figure 6:
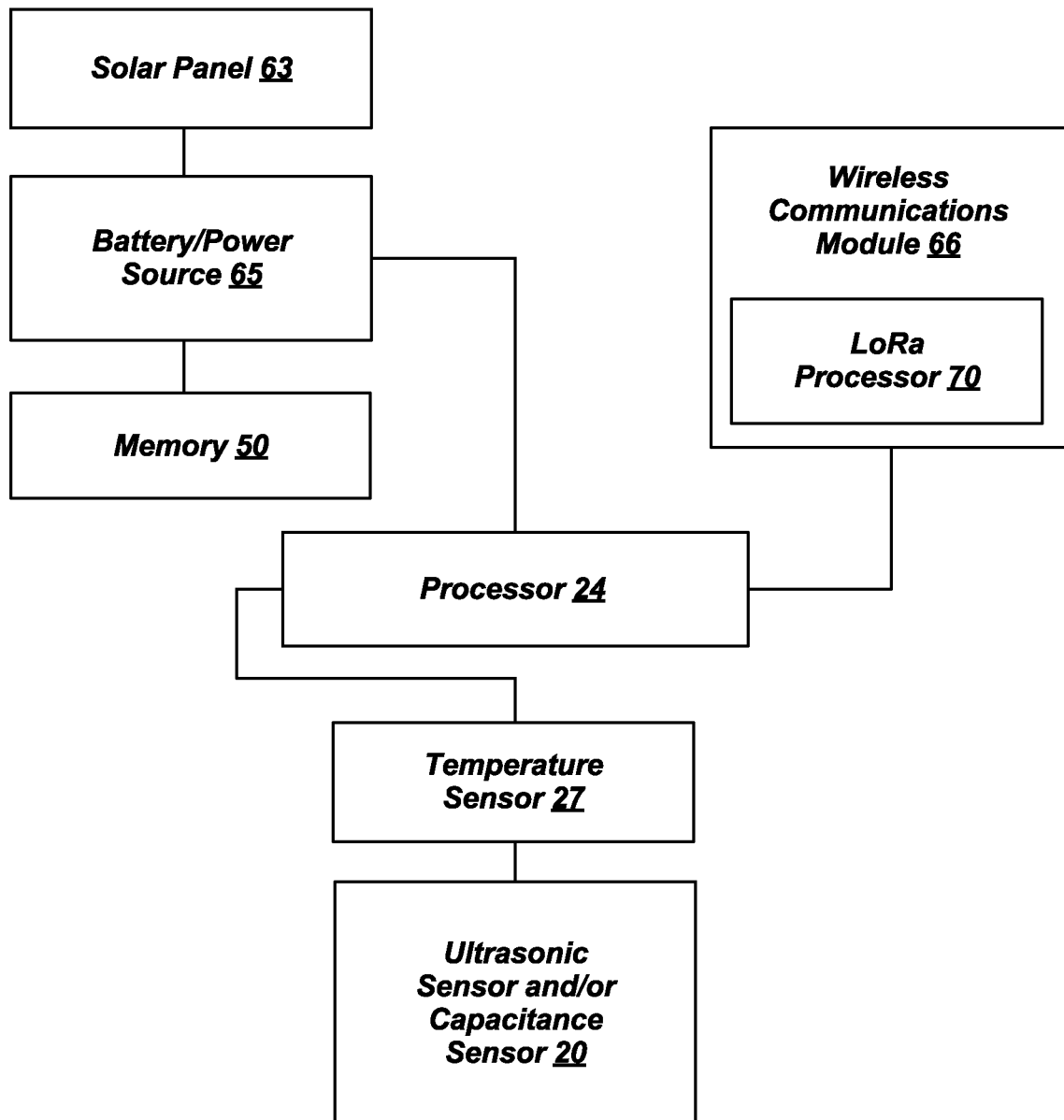
FIG. 6 is a block diagram of exemplary hardware that may be used in an in-ground soil moisture sensor as disclosed herein.

The sensor housing 12 may also be provided with one or more openings for receiving sensors. For example, as seen in FIGS. 3-5, the sensor housing 12 may be provided with one or more upper openings 40a, 40b for receiving one or more sensors. The upper opening(s) 40 may be more proximal to the upper end 38 of the housing. In the specific configuration shown in FIGS. 3-5, two upper openings 40a, 40b are provided. In other configurations, a single upper opening or multiple openings such as 2, 3, 4, etc. may be provided. In yet other configurations, the housing 12 may not include openings for upper sensors. Any openings provided in the housing may extend from the inner side 32a to the outer side 32b of the wall 32 of the sensor housing 12 (FIG. 5).

The sensor housing 12 may also be provided with one or more central openings for receiving sensors. For example, best seen in FIGS. 4-5 and FIG. 12B, the sensor housing 12 may be provided with one or more central opening(s) 44 for receiving one or more sensors. In the specific configuration shown in FIGS. 3-5, a single central opening 44 is provided and may receive a temperature sensor 27. Temperature sensor(s) 27 may provide an accurate ground understanding of soil heat and freezing events, and may be in communication with one or more processors as detailed below to communicate the soil temperature.

In other configurations, multiple central openings 44 such as 2, 3, 4, etc. may be provided to receive any type of sensor desired. In yet other configurations, the housing 12 may not include openings for centrally-placed sensors. Any openings provided in the housing 12 may extend from the inner side 32a to the outer side 32b of the wall 32 of the sensor housing 12. Or, if desired, the openings may extend only partially through the wall 32. In yet other configurations, sensors may be located entirely within the housing and not provided with openings in the outer wall 32 of the sensor housing 12. Placement of the sensors partially or entirely within the housing 12 may serve to protect sensors from harsh environmental conditions. However, one or more openings in the housing wall 32 may allow for more efficient measurements taken by one or more sensors. In yet other configurations, the housing 12 may comprise an acoustically transparent material covering one or more of the upper opening(s) 40, central opening(s) 44, and/or lower opening(s) 47.

Again referring to FIGS. 3-5, the sensor housing 12 may also be provided with one or more lower openings 47 for receiving sensors. In FIGS. 3-5, the sensor housing 12 is provided with two lower openings 47a, 47b for receiving one or more sensors. In other configurations, a single lower opening 47 or multiple openings such as 2, 3, 4, etc. may be provided. In yet other configurations, the housing may not include openings for lower sensors. Any openings provided in the housing may extend from the inner side 32a to the outer side 32b of the wall 32 of the sensor housing 12, or may extend only partially through the housing wall 32. Any type of sensor desired may be placed within the opening(s) 47. For example, one or more ultrasonic sensors may be used. Similarly, capacitance sensors and/or temperature sensors, etc. may be used.

According to another aspect, the housing 12 may also comprise one or more removable covers for attachment to the upper end 38 of the housing 12. In one configuration, the housing 12 may be provided with a first removable cover 55 for use during installation as detailed below, and a second removable cover 60 for placement after the sensor 10 is installed. The removable covers 55, 60 may be placed over the upper end 38 of the housing. In other configurations, the cover may be non-removable and/or integral to the housing 12.

The cover 60 may include one or more solar panels 63 or photo-voltaic modules for converting sunlight to power. The solar panel(s) 63 and cover 60 may be designed to withstand various types of weather events, such as extreme heat and freezing, as well as extreme wet and dry conditions. Additionally, the solar panel(s) 63 and cover 60 may be designed to withstand outdoor landscaping events, such as mowing, aeration, etc. The solar panel(s) 63 may be in electrical communication with a power source 65. According to one aspect, the solar panel(s) 63 being built into the cover 60 may also allow for more powerful wireless communication for the wireless communications module 66. For example, known transparent or nearly transparent solar panels may be used that effectively capture light rays needed to generate power, and at the same time present little barrier for wireless signals to pass through. In other configurations, the solar panel(s) 63 may be provided for separate from the cover 60.

In one example, power may be provided to the power source 65 using a thermoelectric cooler, or TEC or Peltier device. Thermoelectric cooling uses the Peltier effect to create a heat flux at the junction of two different types of materials. Because the sensor 10 is buried in the ground and also exposed to the air, TEC can be used to create a heat flux between the portion of the device in the ground and the portion exposed to the air and generate electricity, which can be stored in power source 65 and used to power the sensor 10.

According to another aspect, the cover 60 may be interchangeable to customize the sensor 10 based on unique needs for the function of the sensor 10. For example, a specific location for the sensor 10 or type of soil that the sensor must be placed in, etc. Types of customizable covers 60 can include a larger power bank, a larger antenna, etc. This can allow the user/client to continue to use the same sensor 10 for an extended period of time, changing the cover 60 as necessary while keeping the same housing 12. In other configurations, the cover 60 may be integral to the housing 12 and/or non-interchangeable.

Power source 65 may include one or more batteries, including a battery with efficient and extended life. For example, the solar panel(s) 63 may recharge the internal power source 65 providing for a lifetime of over five years for the soil moisture sensor 10, even with updates and battery drain. Or a TEC may recharge the internal power source 65, or any other suitable source of power can be used. A power source 65 that does not require electrical wiring to a mains power source may have several advantages over traditional moisture sensors that are hard-wired for power. For example, installation is simplified and placement of the moisture sensor 10 is not limited to areas that can be hard-wired only. Any suitable power source 65 may be used and in some configurations a rechargeable lithium-ion battery may be used for wireless operation.

In some configurations, the power source 65 may selectively power the processor 24, and/or one or more of the sensors and wireless communications modules. The power source 65 may be provided with its own processor. For example, the power source 65 may selectively power the moisture sensor 10 once per hour to take measurements from the sensors which are received and/or processed by the processor, and communicated by the wireless communications module. Or the power source 65 may selectively power the moisture sensor once every 2, 3, 4, 5, 6, 12, or 24 hours, etc. Other events may also be used to trigger selective powering of the moisture sensor 10. For example, the moisture sensor 10 may be powered at the same time as a watering event (such as a scheduled watering) and remain on for a particular pre-determined duration during or after the watering event. Or the moisture sensor 10 may be powered after a pre-determined duration after the watering event. Similarly, the moisture sensor may turn on in response to a main controller receiving information relating to a weather event and may remain on for a pre-determined duration of time during or after the weather event, such as a precipitation event. In other configurations, the moisture sensor 10 may continuously or nearly continuously take measurements of the temperature, soil moisture, etc., and wirelessly transit the measurements received.

The processor 24 may also be located within the housing 12, and may be in communication with one or more sensors, such as ultrasonic sensors, temperature sensors, capacitance sensors, transducers, etc. Processor 24 can be a PCB, and may include one or more known processing devices, such as microprocessors manufactured by Intel™, NVIDIA™, or various processors from other manufacturers. The disclosed embodiments are not limited to any specific type of processor. The processor may also be in communication with memory 50. Memory 50 may include one or more storage devices configured to store instructions used by processor 24 to perform functions related to disclosed embodiments.

Memory 50 may be configured with one or more software instructions, such as programs that may perform one or more operations when executed by processor 24. The disclosed embodiments are not limited to separate programs or computers configured to perform dedicated tasks. For example, memory 50 may include a single program that performs the functions of the processor 24, or memory 50 may comprise multiple programs. Memory 50 may also store data that is used by one or more programs, and/or an irrigation controller 140 (see description with respect to FIG. 14, below). In some configurations, memory 50 and associated applications may be stored within the sensor housing 12, and in other configurations, memory 50 and associated applications may be stored at the irrigation controller 140 for storage and processing by the irrigation controller 140 and/or in the cloud, such as network 58 as described in more detail below.

The processor 24 may also be in communication with one or more wireless communications modules 66. The wireless communications module 66 may be any suitable wireless communications module known in the art, such as satellite communication, low-range wireless communication, Bluetooth, WiFi, infrared communication, Bluetooth Low Energy, WiMax, etc. In some configurations, LoRa technology may be used. LoRa (short for long range) is a spread spectrum modulation technique derived from chirp spread spectrum (CSS) technology. LoRa devices and wireless radio frequency technology use a long range, low power wireless platform that has become widely used for Internet of Things (IoT) networks. Any suitable wireless communication may be used to allow for extended connection across a wide geographical area. For example, the wireless communications module 66 may comprise an antenna 68, such as an SMA antenna connector or any other suitable antenna, and a wireless communications processor 70. The wireless communications module 66 may allow for the processor 24 to communicate sensor data to a central irrigation controller, and also may allow the moisture sensor 10 to receive data from the central irrigation controller.

In configurations of moisture sensors that utilize one or more ultrasonic sensors 20, the ultrasonic sensor(s) 20 may measure soil properties by generating an ultrasonic signal and detecting all reflected signals through the soil the ultrasonic signal passes through. Mapping these reflected signals against the time of flight (TOF) or the time it takes for the acoustic wave to propagate through the soil and return to the transducer as a reflection or echo allows for the generation of an acoustic signal snapshot or frame from that transducer, where the y-axis is the amplitude of the echo, and the x-axis is the TOF. The acoustic signals captured by ultrasonic sensor(s) 20 are capable of differentiating changes in the soil moisture levels, and can give other data relating to the soil, such as composition of the soil.

The processor 24 may send raw data collected by the ultrasonic sensor(s) 20 to an irrigation controller for processing, or the processor 24 may further process the raw data, to determine the moisture within the soil. For example, a reflectance wave analyzer module 150 (FIG. 14, described in more detail below) may be provided to process the raw data detected by the ultrasonic sensor(s) 20. Processing of the raw data includes variables for consideration into any moisture content equation, such as soil type, rocks, air gaps within the soil, organic material such as plant roots, etc. Baseline data established for a variety of soil types may be used in processing the data (for example, baseline data may be provided for dry soil types, over-saturated soil types, etc.). Known data processing techniques, such as look-up tables, etc., can be used in processing the data. Differences in reflection/absorption of the ultrasonic signal through the soil indicate the amount of water in the soil. Variables factored into the calculation of water in the soil include soil type, rocks, air gaps, organic materials (roots), etc.

Figure 7:
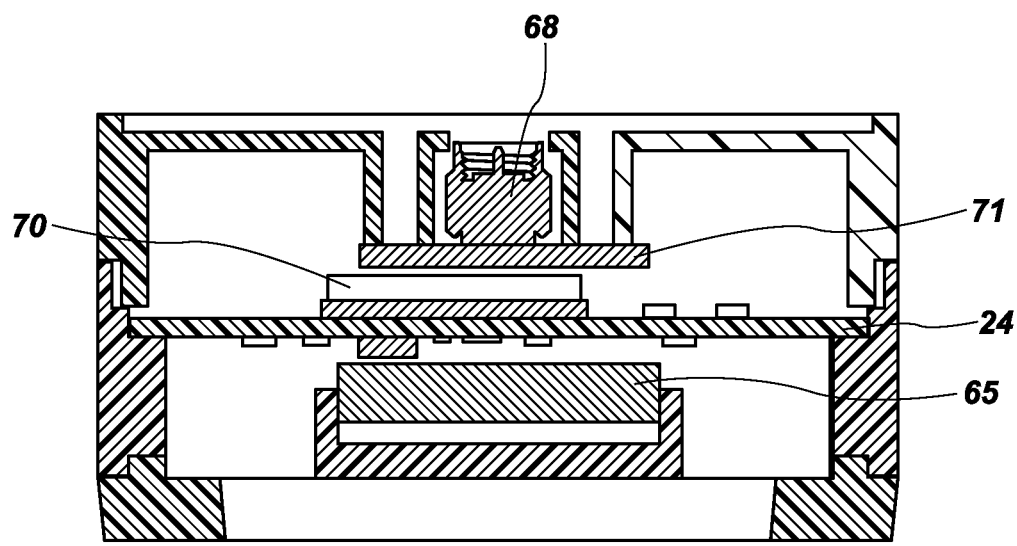
FIG. 7 is a cross-sectional view of an exemplary upper portion of an in-ground soil moisture sensor with the cover removed.

With reference to FIG. 7, a cross-sectional view of the upper end 38 of an exemplary soil moisture sensor is shown. An antenna connector 68 allows a separate antenna for communication to be attached at the upper end of the sensor. In this exemplary sensor, the antenna connector 68 is in electrical communication with a processor, such as a PCB, 71. The configuration of FIG. 7 provides separate processors/PCBs for the main operations and for power and/or antenna communications. Processor 24 is provided for the main operations of the sensor. In other configurations, fewer or more PCBs can be used. Also shown in FIG. 7 is a LoRa processor 70 in electrical communication with the processor 24, and a power source 65 such as a lithium ion battery.

Figure 8:
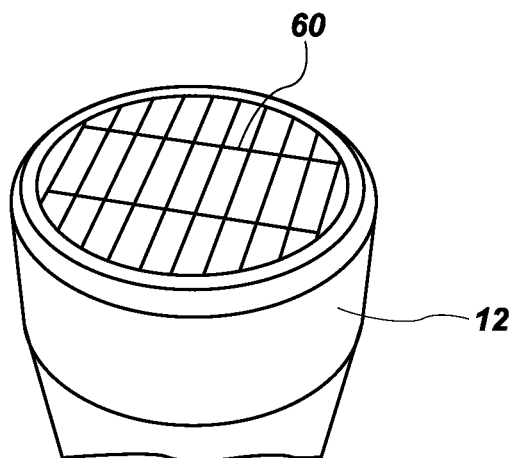
FIG. 8 is a perspective view of an exemplary upper portion of an in-ground soil moisture sensor with the cover in place.
Figure 9:
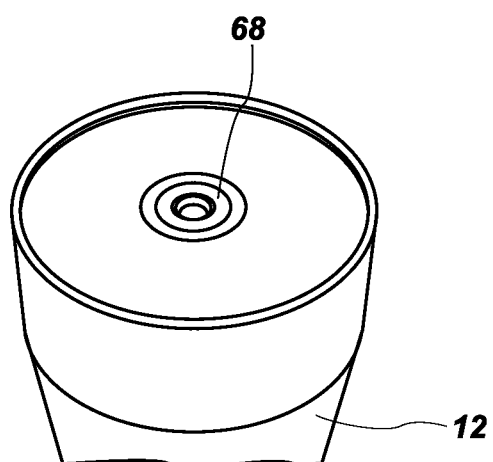
FIG. 9 is a perspective view of the exemplary upper portion of an in-ground soil moisture sensor of FIG. 8 with the cover removed.
Figure 10:
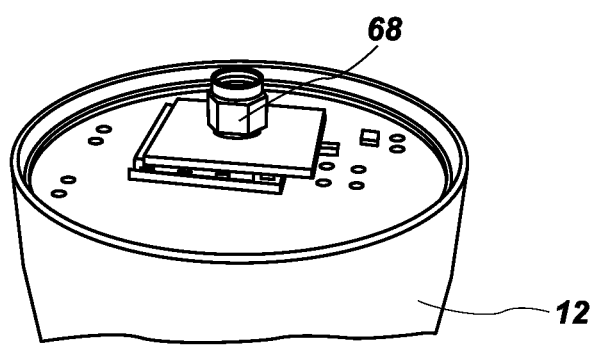
FIG. 10 is a perspective view of the exemplary upper portion of an in-ground soil moisture sensor of FIGS. 8-9 with the cover removed and plastic housing top portion removed, exposing the processor and antenna.

FIGS. 8-10 show examples of the upper end 38 of the sensor, with the solar cap in place (FIG. 8), the solar cap removed with the exposed antenna connector 68 (FIG. 9), and the solar cap and top of housing removed (FIG. 10). FIG. 8 shows a top, perspective view of an exemplary moisture sensor with a solar cap 60a in place on top of housing 12. Solar cap 60a is an exemplary cover 60, and other types of covers 60 can also be used. In this example, housing 12 is the shape of an inverted cone, with an upper end 38 that is wider than the bottom or lower end. FIG. 9 shows the same top, perspective view of an exemplary moisture sensor of FIG. 8, but with the solar cap 60a removed and the upper end 38 of the housing 12 exposed. In this view, the antenna connector 68 and power ring are visible. FIG. 10 shows yet another layer removed from the top of the upper end, such that the antenna connector 68 and main controller PCB are exposed.

FIGS. 11A-11B show an example of a moisture sensor that includes a pair of ultrasonic sensors 20, as well as a temperature sensor 27 FIG. 11A shows the electronics separated from the housing, and FIG. 11B shows the electronics in place on the sensor housing. Ultrasonic sensor(s) 20 can provide more data with respect to the soil moisture content compared to a traditional moisture sensor. For example, traditional moisture sensors take the point of measurement only where the sensor is located. Ultrasonic sensors may provide data with respect to the surrounding area and not just the immediate area around the sensor. For example, ultrasonic sensor(s) 20 may detect soil moisture data with respect to the soil from about 30 centimeters away from the moisture sensor 10 up to about 120 centimeters away from the moisture sensor 10. This allows for a much wider soil understanding and better zone data compared to traditional moisture sensors that can only provide local analysis within approximately 2 centimeters of the sensor. An even greater distance can be achieved depending on the type of ultrasonic sensor used.

In one configuration, data inputs taken from temperature sensors, ultrasonic sensors, etc., can be used as inputs for algorithm(s) or logic which outputs a detailed map of the soil, including characteristics for options to landscape the soil and/or irrigate the soil. For example, inputs such as the temperature, moisture, and conductivity of the soil can be taken by a sensor 10. These inputs can be communicated to a processor and used to determine the appropriate care and maintenance of the soil. In one configuration the users can each upload their data regarding individual sensors to a centralized controller for analysis and further communications to a user/client.

Figure 12A:
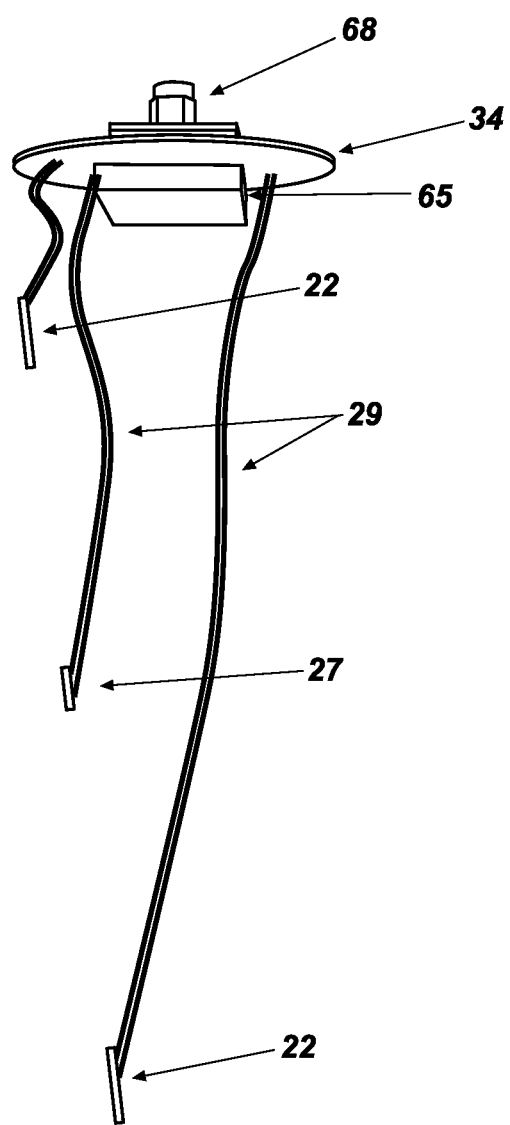
FIG. 12A is a front view of the electronics of another exemplary sensor, with the housing removed for clarity to show placement of the electronics relative to the housing.
Figure 12B:
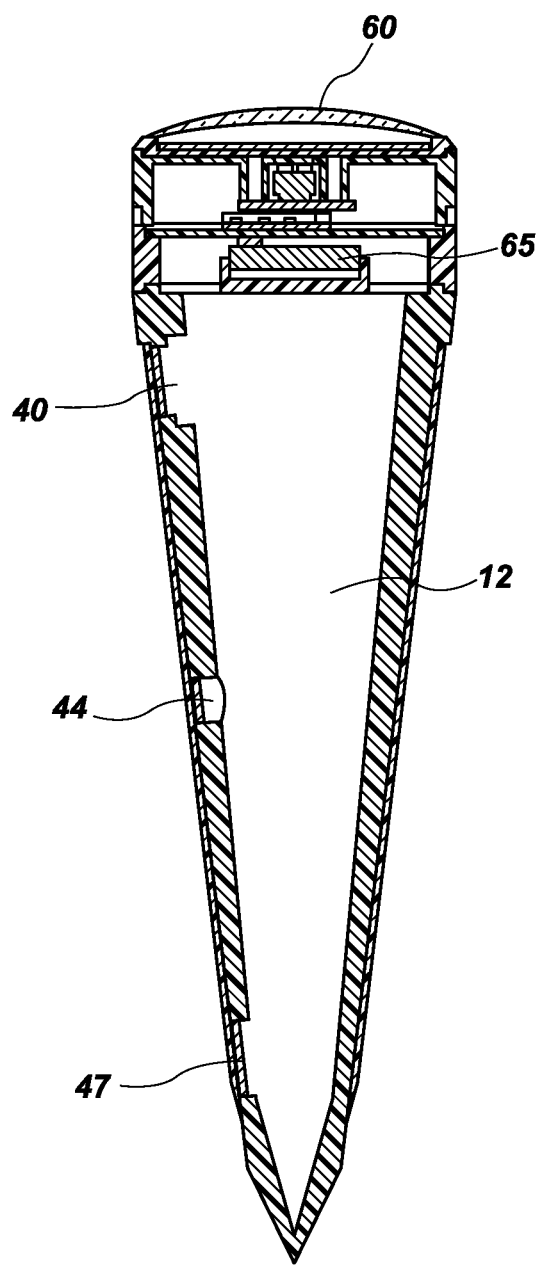
FIG. 12B is a front, cross-sectional view of the exemplary sensor of FIG. 12A sensor using capacitance sensors.

In other configurations, traditional capacitance sensors 22 may be used (see FIGS. 12A-12B). FIGS. 12A-12B show an example of a moisture sensor that includes a pair of capacitance sensors 22, as well as a temperature sensor 27 FIG. 12A shows the electronics separated from the housing, and FIG. 12B shows the electronics in place on the sensor housing. Wiring 29 can be used to connect one or more sensors to the main PCB or controller 34 of the soil moisture sensor 10.

In use, a soil moisture sensor 10 may first be selected with the desired features, such as the desired number and types of sensors, size, etc. Determining the desired features of the soil moisture sensor may depend on the placement of the sensor 10 with respect to a central controller as well as the options for power and soil type. FIGS. 13A-13B includes an exemplary flow diagram of installation steps for a soil moisture sensor 10. An optional first step (105) may be to drill an initial depth hole. This step is not necessary and may be omitted depending on the particulars for the unique installation, such as soil type and depth of installation desired. The soil moisture sensor 10 may be fitted with a first removable cover 55, such as a rubber cap. The soil moisture sensor 10 may be provided with this installation-type cover when it is manufactured, or the user may first place the cover 55 onto the soil moisture sensor 10. The installation-type cover 55 may protect the soil moisture sensor during installation. And by having more sensitive portions of the sensor, such as solar panels and/or wireless modules, not in place during installation, it may ensure these more sensitive portions are not damaged during installation.

The soil moisture sensor 10 may then be hammered or otherwise fitted in place (110). For example, with the protective rubber cover 55 in place, the rubber cover 55 may be directly hammered until the soil moisture sensor 10 reaches the desired depth. In some configurations, it may be desirable to install the soil moisture sensor 10 so it is flush or nearly flush with the ground. In other configurations, it may be desirable to install the soil moisture sensor 10 so it is slightly elevated from the ground. In either case, the soil moisture sensor 10 may be placed at the desired height with respect to ground (flush 120a or exposed 120b).

After the soil moisture sensor 10 is at the appropriate depth in the ground, the rubber cover 55 may be removed (115), and the cover for use of the device, such as a removable cover 60 provided with one or more solar panels, may be placed onto the upper end 38 of the housing 12, with the cover either flush with the ground (120a) or exposed (120b). Removable cover 60 may be a standard cover or may be selected or configured for a particular use, depending on the location of the soil moisture sensor within an irrigation system and the desired functionality of the soil moisture sensor within the irrigation system. In some configurations, the antenna portion of the soil moisture sensor may also be installed after the device is inserted into the ground to ensure no damage to the antenna during installation.

Figure 14:
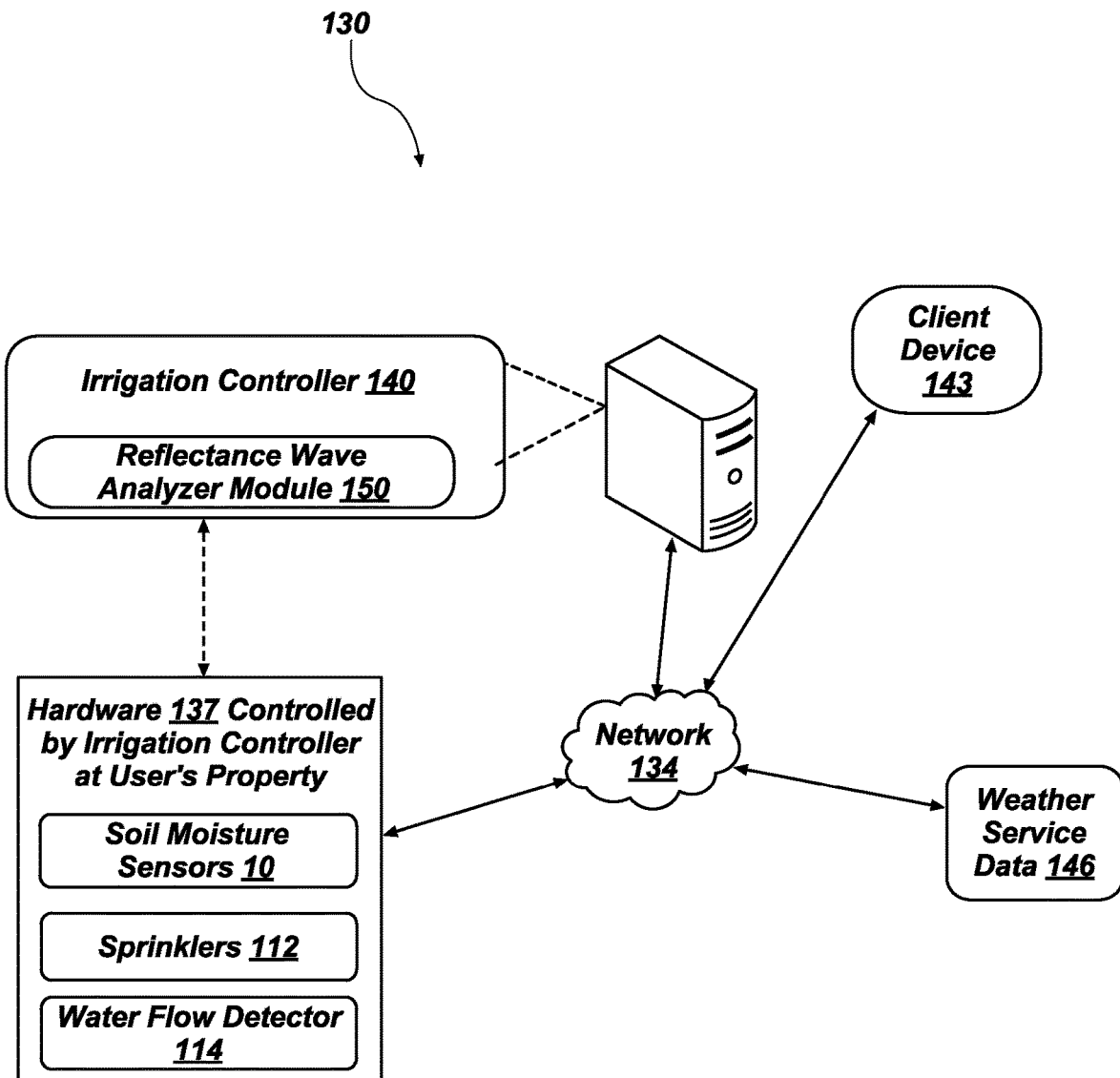
FIG. 14 is a block diagram of an exemplary extended irrigation network in which an in-ground soil moisture sensor may be employed.

Once in place, the soil moisture sensor 10 may begin to detect soil moisture levels and communicate them to a central source, such as a centralized irrigation controller 140. FIG. 14 is a block diagram of one embodiment of a system 130 for soil moisture sensing and related irrigation control. The system 130 may generally include a network 134 to allow communications between hardware 137 (such as soil moisture sensors 10), an irrigation controller 140, a client device 143, and optionally one or more databases, such as a weather service database 146. In some configurations, the irrigation controller 140 is on-site or proximal to the landscape that it controls. The irrigation controller 140 may contain the programming for the reflectance wave analyzer module 150, or in other configurations, the programming for the reflectance wave analyzer module may be stored in the cloud or at another remote location and in communication with the controller 140.

Reflectance wave analyzer module 150 may collect the ultrasonic signals captured by the sensor(s) 10 and provide the analysis of the data to determine soil moisture levels. For example, the reflectance wave analyzer module 150 may be programmed with pre-determined baseline data, look-up tables, etc., to compare the received values to the pre-determined baseline data. Further, various types of soils may be used to generate a set of pre-determined baseline data for accurate comparison. For example, pre-determined baseline data and expected reflectance values for moisture levels of different types of soils may be stored within a memory and the reflectance wave analyzer module may query the memory to determine the soil moisture level associated with the baseline levels. In other configurations, the reflectance wave analyzer module 150 may be provided with machine learning, such that the algorithms used to determine the soil moisture level improve automatically by use of the data.

In one embodiment, client devices 143 may take the form of mobile computing devices such as smartphones or tablets, general purpose computers, or any combination of these components. Alternatively, client devices 143 (or systems including client devices 143) may be configured as a particular apparatus, embedded system, dedicated circuit, and the like based on the storage, execution, and/or implementation of the software instructions that perform one or more operations consistent with the disclosed embodiments. According to some embodiments, client devices 143 may comprise web browsers or similar computing devices that access a web site, for example with web-based software, consistent with disclosed embodiments. In one implementation the system 130 is connected to one or more client devices 143-1, 143-2, 143-3, etc., individually and commonly referred to as client device(s) 143 hereinafter, through a communication network 134. Multiple client devices 143 may allow multiple users, such as owners, landscaping companies, etc., to each have access to data relating to the property.

The client devices 143 may be used to allow clients to provide specific watering instructions to the irrigation controller 140, to inform and/or alert the client about watering steps taken by the irrigation system, and/or to inform the client about the state of the irrigation system, including real-time soil moisture levels. The client devices 143 may serve both to provide specific instructions regarding watering, and to provide the client with the real-time status of the system and the temperature and/or soil moisture levels as measured by each soil moisture sensor 10. Such client devices 143 include, but are not limited to, desktop computers, hand-held devices, laptops or other portable computers, tablet computers, mobile phones, PDAs, smartphones, smart energy meters, smart home monitoring systems, smart electric appliances, and the like. Further, the client devices 143 may include devices capable of exchanging data to provide connectivity to different communicating devices and computing systems. Such devices may include, but are not limited to, data cards, mobile adapters, wireless (WiFi™) adapters, routers, a wireless modem, a wireless communication device, a cordless phone, a wireless local loop (WLL) station, and the like. The components of client devices 143 may be implemented in hardware, software, or a combination of both hardware and software, as will be apparent to those skilled in the art.

Although the foregoing disclosure provides many specifics, including application of the sensors with respect to moisture sensing, these should not be construed as limiting the scope any of the ensuing claims. For example, the disclosure may also be applied to sensing water flow, moisture, plant life, and more. Other embodiments may be devised which do not depart from the scopes of the claims. Features from different embodiments may be employed separately or in combination. Accordingly, all additions, deletions and modifications to the disclosed subject matter that fall within the scopes of the claims are to be embraced thereby. The scope of each claim is indicated and limited only by its plain language and the full scope of available legal equivalents to its elements.

I claim:

1. A system for analyzing soil moisture levels, the system comprising:
    a sensor housing having an upper end and a lower end to be inserted into soil;
    an upper environmental sensor located in the sensor housing at an opening for the upper environmental sensor, wherein the upper environmental sensor includes an upper moisture sensor;
    a lower environmental sensor located in the sensor housing, wherein the lower environmental sensor includes a lower moisture sensor, wherein the lower environmental sensor is located closer to the lower end than the upper environmental sensor and the upper environmental sensor is located closer to the upper end than the lower environmental sensor;
    a wireless communications module in communication with the sensor; and
    a power source located in the sensor housing.

2. The system of claim 1, wherein the sensor housing is hollow.

3. The system of claim 1, wherein the upper environmental sensor includes at least one of an ultrasonic moisture sensor, a capacitance moisture sensor, or an ultrasonic transducer.

4. The system of claim 1, wherein the upper environmental sensor is a different type of sensor than the lower environmental sensor.

5. The system of claim 4, wherein the sensor housing further includes a temperature sensor.

6. The system of claim 1, wherein the upper environmental sensor extends at least partially through the opening.

7. The system of claim 1, wherein the sensor housing includes a cover, and further comprising a solar panel on the cover, the solar panel connected to the power source.

8. The system of claim 1, wherein the power source includes a thermoelectric cooler.

9. The system of claim 1, wherein the power source includes a battery.

10. The system of claim 1, wherein the upper environmental sensor and the lower environmental sensor are wirelessly connected, using the wireless communications module, to a remote computing device.

11. A method, comprising:
    receiving upper environmental sensor measurements from an upper moisture sensor including an upper environmental sensor;
    receiving lower environmental sensor measurements from a lower moisture sensor including a lower environmental sensor;
    determining a soil moisture level for an area surrounding the moisture sensor, the soil moisture level including a change in the soil moisture level between the upper measurement and the lower measurement; and
    wirelessly transmitting the soil moisture level to a remote computing device.

12. The method of claim 11, wherein at least one of the environmental sensor or the lower environmental sensor is an ultrasonic sensor, and further comprising generating, using the ultrasonic sensor, an ultrasonic signal, and wherein determining the soil moisture level includes receiving reflected ultrasonic signals based on the ultrasonic signal.

13. The method of claim 12, wherein determining the soil moisture level includes comparing the reflected ultrasonic signals to baseline data, the baseline data including expected reflectance values of the reflected ultrasonic signals, the expected reflectance values associated with moisture levels of different types of soils.

14. The method of claim 13, wherein determining the moisture levels includes determining the moisture levels based on the reflected ultrasonic signals and at least one of soil type, rocks, air gaps, or organic materials.

15. A system for analyzing soil moisture levels, the system comprising:
 a sensor housing having an upper end and a lower end to be inserted into soil;
 an upper environmental sensor located in the sensor housing at an opening for the upper environmental sensor, wherein the upper environmental sensor includes an upper moisture sensor;
 a lower environmental sensor located in the sensor housing, wherein the lower environmental sensor includes a lower moisture sensor, wherein the lower environmental sensor is located closer to the lower end than the upper environmental sensor and the upper environmental sensor is located closer to the upper end than the lower environmental sensor;
 a wireless communications module in communication with the sensor; and
 memory with instructions stored thereon that cause a processor to:
  receive sensor measurements from the upper environmental sensor and the lower environmental sensor; and
  transmit the sensor measurements to a remote computing device using the wireless communications module.

16. The system of claim 15, wherein the memory further includes instructions which further cause the processor to, based on pre-programmed baseline data, determine a soil moisture level for an area surrounding the sensor using the sensor measurements.

17. The system of claim 16, wherein transmitting the sensor measurements includes transmitting the soil moisture level to the remote computing device.

18. The system of claim 15, wherein the sensor housing includes a cover, and further comprising:
 a power source in the sensor housing, the power source providing power to the upper environmental sensor and the lower environmental sensor, the wireless communications module, the memory, and the processor; and
 a solar panel on the cover, the solar panel connected to the power source.

19. The system of claim 15, further comprising a temperature sensor, and wherein the memory further includes instructions that further cause the processor to:
 receive temperature measurements using the temperature sensor; and
 transmit the temperature measurements to the remote computing device.

20. The system of claim 19, wherein the upper environmental sensor and the lower environmental sensor include capacitance sensors.

* * * * *